United States Patent [19]
Jaser et al.

[11] Patent Number: 5,458,136
[45] Date of Patent: Oct. 17, 1995

[54] ASSEMBLY FOR PRODUCING AEROSOL PULSES

[75] Inventors: Stefan Jaser, Bobingen; Martin Knoch, Berg, both of Germany

[73] Assignee: Paul Ritzau Pari-Werk GmbH, Germany

[21] Appl. No.: 220,595

[22] Filed: Mar. 31, 1994

[51] Int. Cl.$^6$ .................................................. A61M 11/00
[52] U.S. Cl. .................. 128/200.14; 128/200.18
[58] Field of Search ................. 128/200.14, 200.18; 261/79.2; 239/403, 468, 469

[56] References Cited

U.S. PATENT DOCUMENTS

| | | | |
|---|---|---|---|
| Re. 33,717 | 10/1991 | Svoboda | 128/200.18 |
| 1,381,095 | 6/1921 | Starr | 239/468 |
| 3,105,778 | 10/1963 | Anderson | 261/79.2 |
| 3,495,384 | 2/1970 | Alliger | 261/79.2 |
| 3,695,820 | 10/1972 | Hawkes et al. | 239/403 |
| 3,726,634 | 4/1973 | Thomson et al. | 239/403 |
| 3,862,907 | 1/1975 | Shimotsuma et al. | 261/79.2 |
| 4,248,296 | 2/1981 | Jezek | 239/468 |
| 4,434,766 | 3/1984 | Matsuoka et al. | 239/403 |
| 4,512,935 | 4/1985 | Hilmersson et al. | 261/79.2 |
| 5,059,357 | 10/1991 | Wolf et al. | 261/79.2 |

Primary Examiner—Edgar S. Burr
Assistant Examiner—Aaron J. Lewis
Attorney, Agent, or Firm—Merchant, Gould, Smith, Edell, Welter & Schmidt

[57] ABSTRACT

An assembly for producing aerosol pulses with a valve block (1), which has a breathing channel (2), an air channel (3) which enters the breathing channel transversely, and an aerosol channel (4) which enters the breathing channel transversely and mechanical, electromagnetic or pneumatic control valves (S1, S2, R), for controlling the supply of air and aerosol through the channels in the valve block. The assembly has a flow figure (5) in the breathing channel in the area of the openings of the air and aerosol channels. The longitudinal axis of the air channel also is laterally shifted with respect to the longitudinal axis of the breathing channel so that a tangential flow against the flow figure is achieved and that the longitudinal axis of the aerosol channel is laterally shifted with respect to the longitudinal axis of the breathing channel so that a tangential flow against the flow figure is achieved.

16 Claims, 5 Drawing Sheets

5,458,136

ASSEMBLY FOR PRODUCING AEROSOL PULSES

FIELD OF THE INVENTION

The sharp definition of the pulse is essential for the therapeutic or diagnostic application of aerosol pulses which are injected into the patient's breathed air during deep inspiration. For therapy, the effective substance in the aerosol pulse can only be deposited in the desired lung areas if the aerosol pulse is very distinct. The goal in diagnostics is to determine a precise application time point so that a reliable signal and reference size is given for the evaluation of the exhaled air.

An example of a diagnostic application is described in detail hereafter in order to illustrate the application possibilities of aerosol pulses in therapy and diagnostics and to explain the requirements made on the size and distribution over time of the aerosol pulse.

BACKGROUND OF THE INVENTION

For the diagnosis of obstructive ventilation disorders, the lung function can be tested via the analysis of exhaled aerosol boll as described by T. Beinert et al in Pneumologie 44 (1990), Supplement 2, 1026. In this, one takes advantage of the fact that monodisperse inert aerosol particles with a given small diameter behave for the most part like a non-diffuse gas and can therefore be used as a marker for the convective gas transport. If such an aerosol is injected into the breathed air and inhaled as a low volume bolus, i.e. 20 cm$^3$, then one can read the convective exchange of air volume between intrapulmonary residual air and inspired air via the volume in which the aerosol particles in the exhaled air are distributed. The shape and position of the exhaled bolus have changed with respect to the inhaled one. The measurement of the particle concentration as a function of the breathed volume is done via a continuously recording aerosol photometer and by using a monodisperse aerosol made of inert sebacic acid di(2-ethylhexyl) ester droplets (DEHS) for example.

The known measurement device consists of a valve block in which there is a breathing channel, an air channel and an aerosol channel. Inhalation and exhalation pass through the breathing channel, fresh air passes through the air channel and the aerosol passes through the aerosol channel. Control valves that control the supply of air and aerosol in the breathed air are part of the valve block. The control valves for air and aerosol are mechanical, electromagnetic or pneumatically operated so that during an inhalation phase the supply of fresh air is interrupted and can be replaced momentarily by the supply of aerosol. During this short switch over, an aerosol pulse is injected into the breathed air.

A typical breathing maneuver is shown in FIG. 8A; ascending curves correspond to the inspiratory phase E, descending curves to the expiratory phase A. During a deep inspiratory phase $E_t$, a given air volume $V_i$ (i.e. 1 liter) is inhaled from FRC at a given volume flow (i.e. 250 cm$^3$/s). In this phase an aerosol bolus $B_i$ is injected into the breathed air and the aerosol is inhaled by the patient. An aerosol bolus $B_e$ appears in the exhaled air during the deep expiratory phase $A_t$ which follows the deep inspiratory phase.

The exhaled bolus $B_e$ is compared to the inhaled bolus $B_i$ for analysis as shown schematically in FIG. 8B. To characterize the dispersion, the positional shift and shape of the exhaled bolus is determined. The dispersion H is determined via a ratio of the half-width $H_{50}$ of the inhaled and exhaled boll as per the equation $$H=(H_{50e}^2-H_{50i}^2)^{1/2}$$

The dispersion is a standard for the increase in volume in which the aerosol particles are distributed in the exhaled air. It describes the convective exchange between the intrapulmonary residual air and the inspired air. The positional shift M of the exhaled bolus is also determined with reference to the aerosol bolus in the inhaled air by the equation $$M=V_e-V_i$$

One assumes a symmetrical concentration curve for the inhaled bolus. The asymmetry of the exhaled bolus is evaluated using shape deformation factors.

This example makes it clear how dependent therapy and diagnostics are on the quality of the aerosol pulse which is injected into the breathed air. Specifically the sharpness, i.e. the steepness of slope and the maximum achieved concentration of the aerosol pulse play a decisive role.

SUMMARY OF THE INVENTION

The purpose of the invention is to create an assembly for the production of aerosol pulses that, due to their sharpness, are well suited for aerosol application in lung function diagnostics and therapy. The invention includes a valve block having a breathing channel, an air channel and an aerosol channel. The air channel and the aerosol channel extend substantially perpendicular to the breathing channel and enter the breathing channel from opposite sides. A flow form or deflector is arranged in the breathing channel in the vicinity of the intersection of the breathing channel with the air and aerosol channels. The longitudinal axes of the air and aerosol channels are shifted relative to each other, so that the fluid flowing through these channels strikes the flow figure tangentially, thus forming a whirling flow around the flow figure. In this way, a very sharply defined flow pulse is created.

BRIEF DESCRIPTION OF THE DRAWINGS

The invention is described in more detail below based on applications and with reference to drawings. The drawings show:

The first preferred embodiment of the assembly is described based on FIGS. 1 to 3. FIG. 1 shows a very simplified view of a valve block of the assembly which is the same for all embodiments and can be seen as the principal constituent of the assembly. FIG. 2 shows the valve block from FIG. 1 in a partially cut view. FIG. 3 shows a switch system which reproduces the valve block in the pneumatic switching with supply lines and valves. Details were avoided as much as possible in FIGS. 1 to 3 so that the illustration is not overloaded and the basic set-up is clarified.

FIG. 1 shows a valve block 1 to which supply lines (not shown) for the supply and valves (also not shown) for controlling the supplied air and the supplied aerosol can be connected. The patient inhales and exhales through a vertical breathing channel 2 whose upper opening 2a serves as the connection point for the supply line. The breathed air flows through the bottom opening 2b of the breathing channel 2 during exhalation. Opening 2b is closed during inhalation. A simple nonreturn valve is suited for this function. However, a controlled electromagnetic or pneumatic valve can also be mounted at the opening 2b of the breathing channel.

Figure 1:
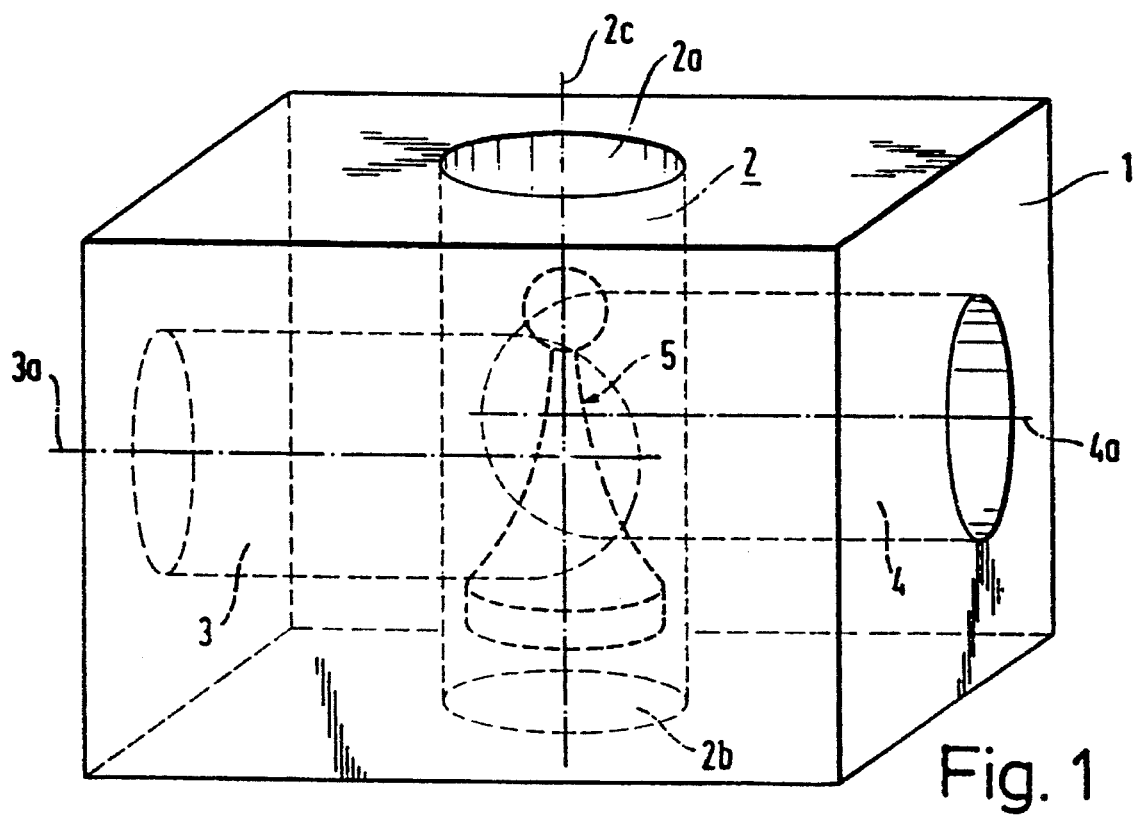
FIG. 1 a simplified perspective view of the basic set-up of a valve block of a first model of the assembly.

An air channel 3, transverse to breathing channel 2 and preferably perpendicular thereto, opens into the breathing channel 2. The air necessary for breathing flows though it to breathing channel 2. The longitudinal axis 3a of the air channel lies laterally adjacent to the longitudinal axis 2c of the breathing channel. An aerosol channel 4, also transverse to breathing channel 2 and preferably perpendicular thereto, opens into breathing channel 2. The aerosol flows through it. As is the case with air channel 3, the longitudinal axis 4a of the aerosol channel lies laterally adjacent the longitudinal axis 2c of the breathing channel however, on the other side of the breathing channel, across from the air channel as shown in FIG. 1. The air channel 3 and the aerosol channel 4 are positioned in such a way that they open into the breathing channel 2 at about the same height. With the perpendicular positioning of the air channel 3 as well as the aerosol channel 4 with respect to the breathing channel, the longitudinal axes 3a and 4a of the air and aerosol channels respectively, are in the same plane. The three channels should preferably be positioned symmetrically to the longitudinal axis 2 of the air channel as shown in FIG. 1. This means that there are three mutually parallel planes, the first with the longitudinal axis 3a of the air channel, the second with the longitudinal axis 2c of the breathing channel and the third with the longitudinal axis 4a of the aerosol channel.

Axially symmetrical flow form 5 influences the air and aerosol flows which are produced in the breathing channel 2. The flow form 5 has a conical portion 5a and an expanded portion 5b at the narrow end of the conical portion. The conical portion 5a has a maximum diameter $d_{5a max}$ and a minimum diameter $d_{5a min}$ that continuously and smoothly blend into each other (that is, without any sharp edges). The maximum diameter $d_{5a max}$ is smaller than the diameter of the breathing channel 2. The maximum diameter $d_{5a max}$ of the expanded portion 5b is larger than the minimum diameter $d_{5a min}$ but smaller than the maximum diameter $d_{5a max}$ of the conical portion 5a of the flow form. The expanded portion 5b is preferably a ball as shown in FIG. 1 or an ellipsoid. The transition between the conical portion 5a and the expanded portion 5b can be varied from that shown in FIG. 1. For example, the conical portion 5a can also blend continuously and smoothly into the expanded portion 5b. A cylindrical portion 5c with a diameter $d_{5c}$ which is the same as the maximum diameter $d_{5a max}$ of the conical portion 5a can be located at the wide end of the conical portion 5a.

Figure 5:
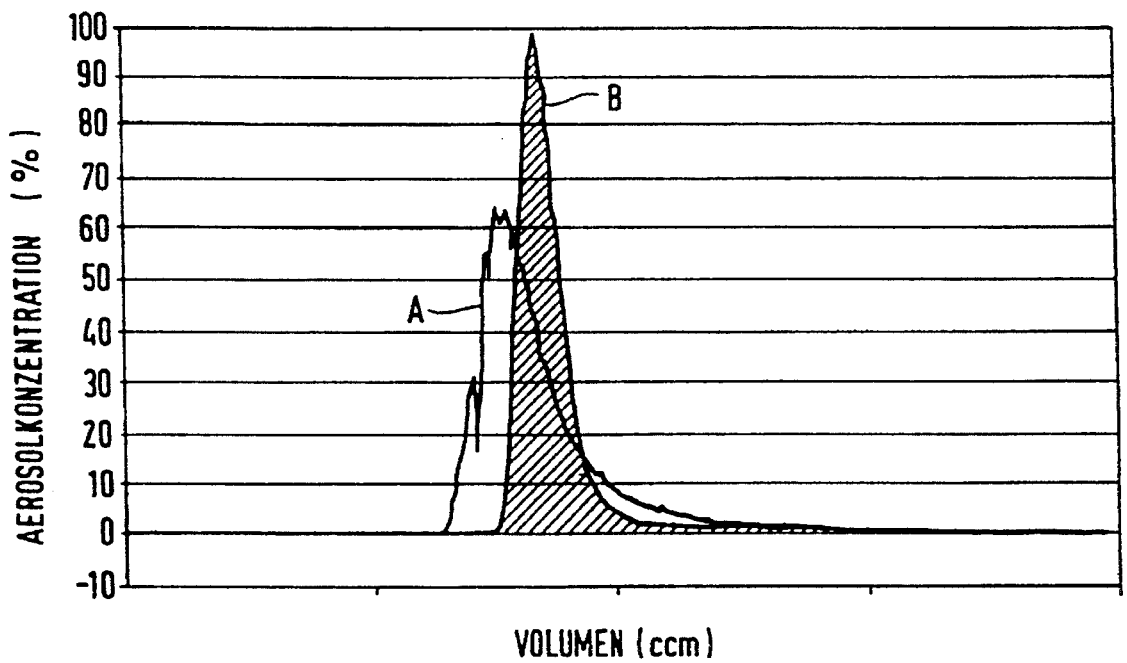
FIG. 5 a calibration curve of the concentration curve of an aerosol pulse produced by conventional methods and one produced by the assembly as per the invention.

The flow FIG. 5 is located in the breathing channel 2 at a position which is at the same height as the openings of the air and aerosol channels. The point of the conical portion 5a points to the opening 2a of the breathing channel and therefore in the direction of the air flow during inhalation. Due to the shifted position of the supply channels 3 and 4, the supplied air and/or supplied aerosol tangentially hits the conical portion 5a of the flow figure.

Due to the shifted longitudinal axis the air coming in through the air channel 3 and/or the aerosol coming in through the aerosol channel 4 hit the flow FIG. 5 on its side whereby a whirl flowing around the flow figure with a rotational speed $V_{rot}$ is produced. At the same time the air and/or aerosol flows toward the flow FIG. 5 in an axial direction with an axial velocity of $V_{ax}$ since the patient inhales through the breathing channel 2.

The ratio of axial and rotational velocity $V_{ax}/V_{rot}$ in the zone of tangential flux is pretty constant for a flow figure having a conical portion. Thus, an even deflection of the flow with minimal duration in the flux area is achieved.

Energy due to the tangential flux is no longer added at the end of the conical portion 5a. This leads to a flow separation with fluid pooling along the wall of the breathing channel 2 immediately downstream from the inlet opening of the air channel 3. The aerosol particles which collect in a ring in this fluid flow away slowly. However, the expanded portion 5b leads to a convective acceleration of the flow in this separation-endangered area whereby pooling of fluid is inhibited and a quick removal of the aerosol particles is ensured.

The ratio of axial to rotational velocity $V_{ax}/V_{rot}$ as well as the direction of rotation of the whirl around the flow FIG. 5 remain unchanged due to the symmetrical positioning of the supply channels 3 and 4 with respect to the axis 2c of the breathing channel 2 even if the flux is changed briefly from the air channel 3 to the aerosol channel 4. Conventional feed techniques would result in a change in the flow status and pooling of fluid. This would result in a delayed transport of the aerosol in the flow profiles which would flatten the ascending and descending flanks as well as the maximum value of the concentration signal of the aerosol bolus.

The separation-free flow diversion as well as the consistent flow conditions under the alternating feed via channels 3 and 4 result in steep ascending and descending flanks of the concentration signal of the aerosol bolus. The flow figure reduces the dead space volume in the breathing channel in the area of the opening of the supply channels, i.e. the volume which must be discharged when changing from supplying air to aerosol.

Figure 2:
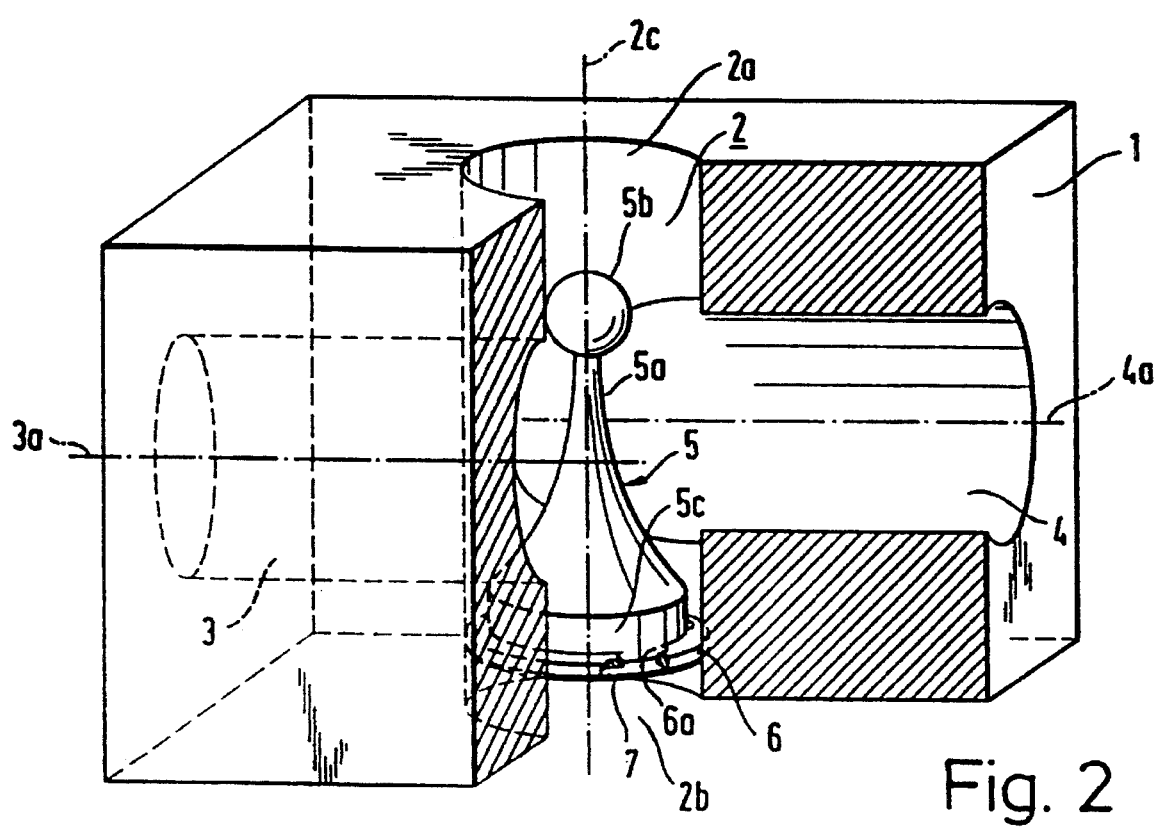
FIG. 2 another perspective but partially cut view of the valve block from FIG. 1 with more details.

Furthermore, FIG. 2 shows that the flow FIG. 5 in the breathing channel 2 is mounted on a flat carrier 6 located at the base of the flow figure and which extends to the inner wall of the breathing channel 2. Arched slits 6a in the carrier 6 enable the breathed air to reach the opening 2b of the breathing channel during exhalation. When the patient exhales into the breathing channel 2, the breathed air flows passed the cylindrical portion 5c of the flow figure and through the slits 6a to the opening 2b of the breathing channel.

A thin elastic disk 7 made of plastic or rubber and with a diameter which essentially corresponds to the diameter of the breathing channel 2 is situated on the side of the flow figure across from the carrier 6. In its resting position, the disk 7 lies on the surface of the carrier 6 due to the elastic forces and closes the slits 6a; during inhalation the elastic forces of the elastic disk 7 are supported by the adjusted pressure ratios. During exhalation the elastic disk 7 lifts off of the surface of the carrier 6 thereby opening the slits 6a of the carrier so that the breathed air can flow out through the opening 2b of the breathing channel.

Figure 3:
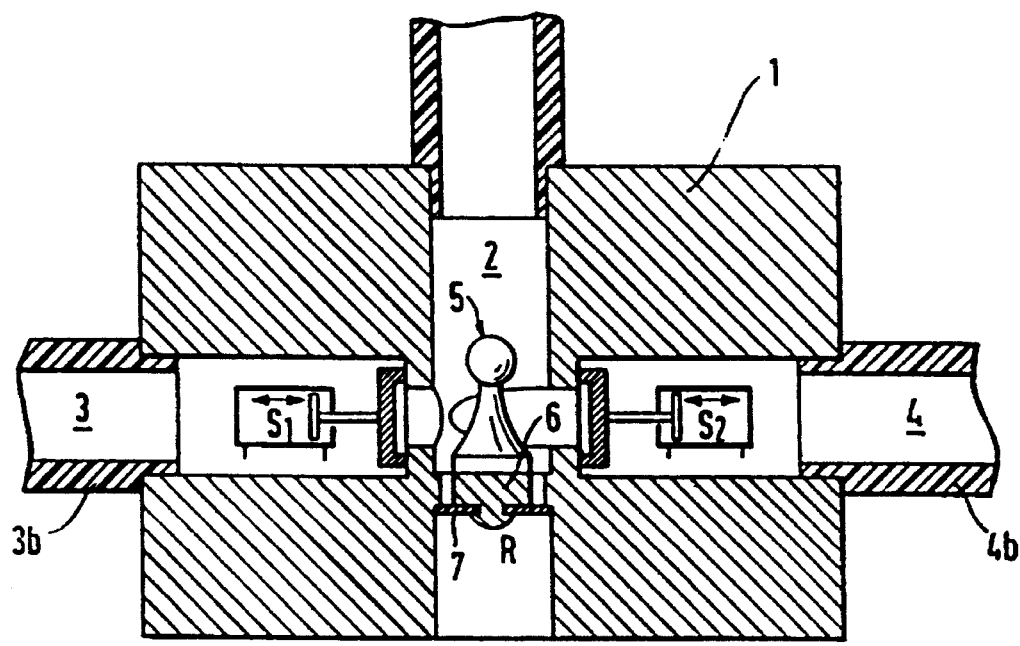
FIG. 3 a cross-sectional view of the valve block from FIG. 1 and 2 with more details in connection with a valve switch system.

In FIG. 3 the valve block 1 is integrated in a switching system which includes a first and second pneumatic control valve S1 and S2 and a nonreturn valve R. The first control valve S1 is located in the air channel 3 and opens/closes the air channel 3 into the breathing channel 2. Likewise, the second control valve S2 is located in the aerosol channel 4 and opens/closes the aerosol channel 4 into the breathing channel 2. The lines by which each of the two control valves are connected to a pneumatic control for time-controlled activation are not shown. The flow FIG. 5, below it the flat carrier 6 (which is shown here in one piece with the valve block 1) and the thin elastic disk 7 which forms the nonreturn valve R are shown at the center of FIG. 3. Air is supplied to the air channel 3 and aerosol is supplied to the aerosol channel 4 via the supply lines 3b and 4b.

The following assumes that, with the help of a nebulizer, a sufficient quantity of a suitable aerosol is made available. A suitable aerosol is, for example, a droplet or particle mist of 10000 round droplets or particles with a diameter of 1 m per 1 $cm^3$ of air.

Figure 4:
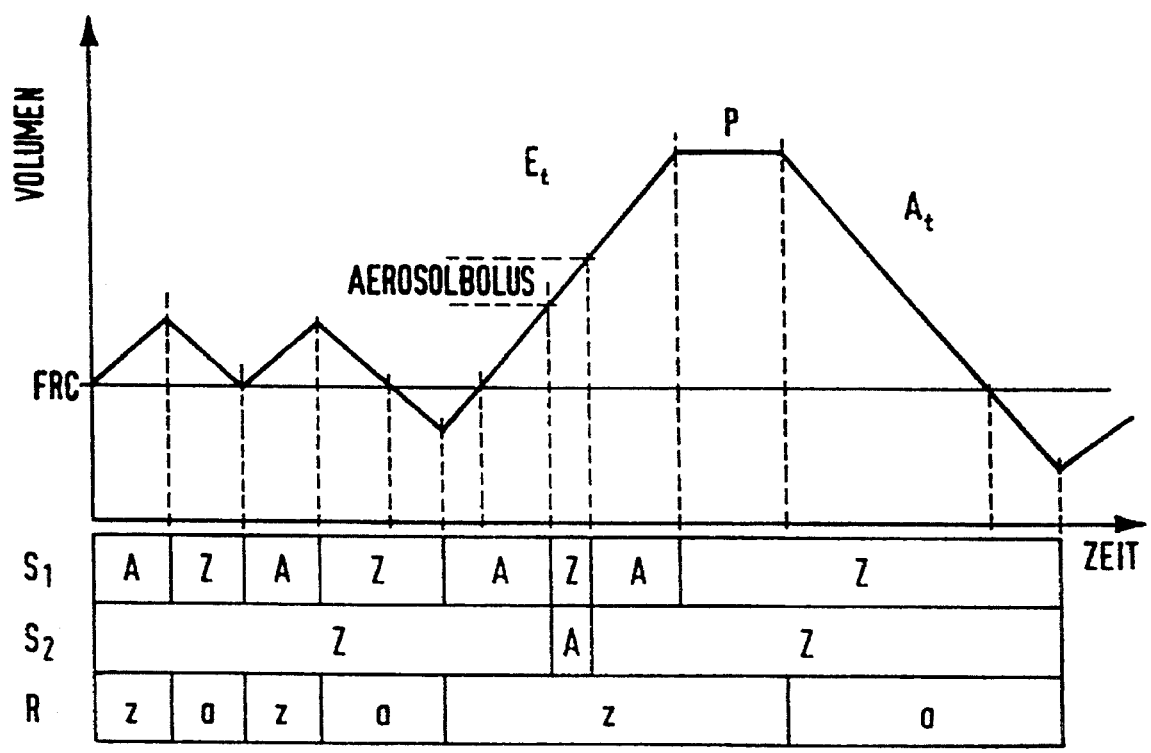
FIG. 4 a diagram of a typical breathing manuver over time and the corresponding switch status of the valves from FIG. 3.

The operation of the first embodiment of the invention is explained based on FIG. 4. The upper part of FIG. 4 illustrates the breathing of the patient. Ascending curves of the breathing curve correspond to the inhalation phases, descending curves to the exhalation phases. During a deep inhalation phase $E_t$, a given air volume at a given volume flow is inhaled from FRC. An aerosol bolus is injected into the breathed air in this phase and the patient inhales the aerosol. A deep exhalation phase $A_t$ follows a pause P.

The lower portion of FIG. 4 shows the switching status of both control valves S1 and S2 as well as of the nonreturn valve R. Capital letters indicate the switching positions forced by the pneumatic control, small letters indicate the switching position of the nonreturn valve due to the pressure ratios. One can see from the diagram that the first control valve S1 is controlled in such a manner that the air channel opens and closes according to the inhalation and exhalation phases. The second control valve S2 is controlled in such a manner that the aerosol channel is usually closed (Z). During the deep inhalation phase and only during the short time of the aerosol pulse, both control valves S1 and S2 are controlled in such a manner that the air channel is closed (Z) and the aerosol channel is open (A).

Since the aerosol pulse produced according to the invention has steep ascending and descending flanks, the time period for the bolus control of both control valves S1 and S2 is comparatively short in order to achieve 100% of the concentration of the prepared aerosol. In the case of the invention, about 0.08 s, corresponding to an aerosol volume of approx. 20 $cm^3$, is sufficient whereas previously about 0.28 s (3.5 times as long) were required in order to achieve 100% of the initial concentration in the aerosol pulse. These interrelations are shown in FIG. 5 which shows the concentration curve of an aerosol pulse produced with a conventional assembly (A) and with the assembly as per the invention (B). The abscissa of the diagram shows the inhaled volume, the ordinate the relative aerosol concentration. Please note that the area under both curves is the same, i.e. corresponds to the same aerosol boll volume. Due to the very steep flank the peak value of process B is 100%, the distribution A however only 60%.

Figure 6:
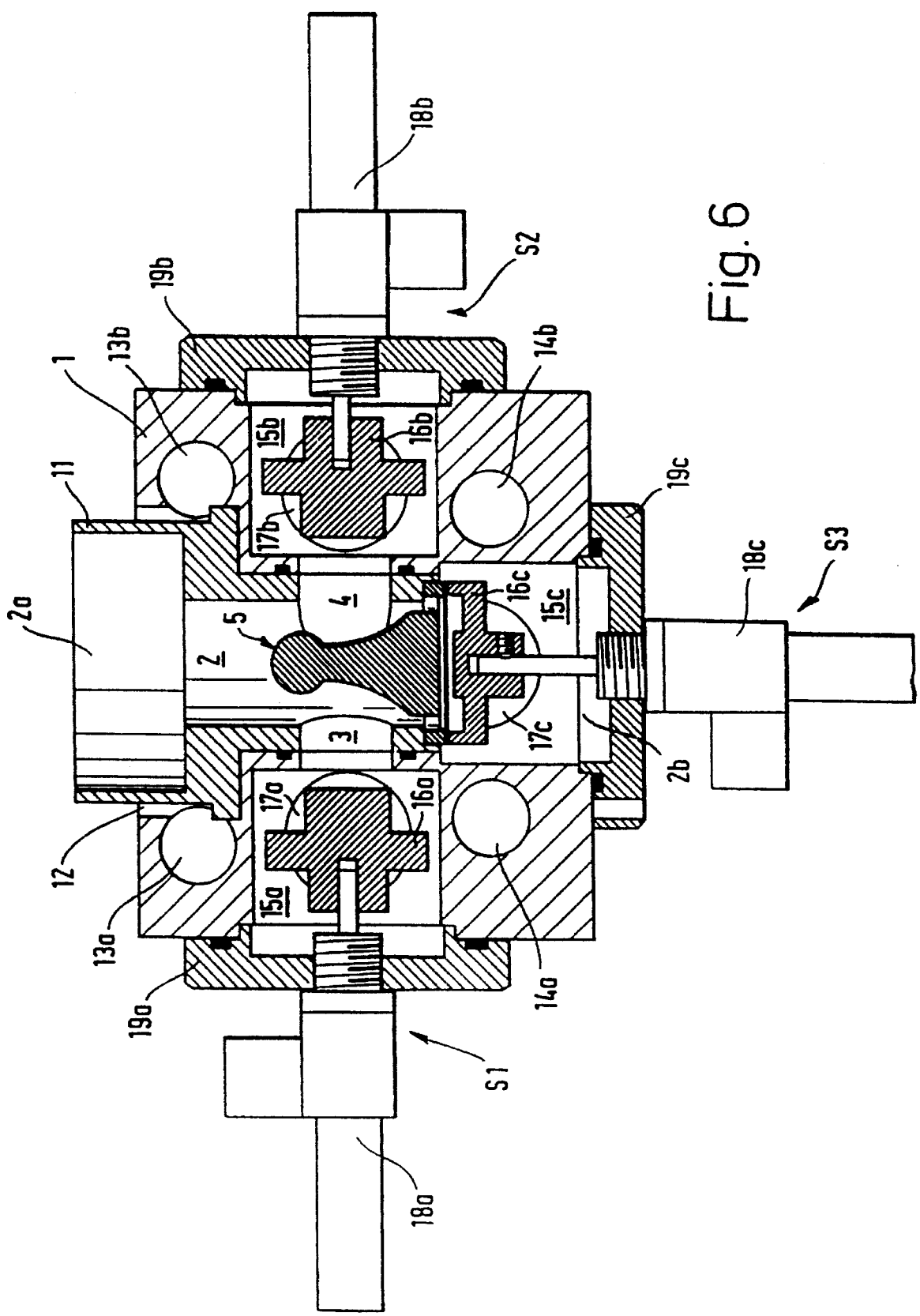
FIG. 6 a cross-sectional view of a second application of the assembly.
Figure 8A:
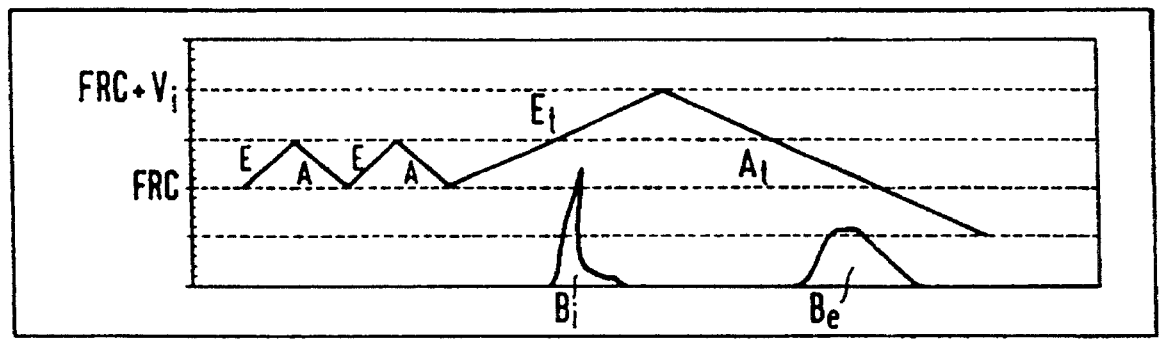
FIG. 8A a diagram illustrating known principles from the field of lung function diagnostics.
Figure 8B:
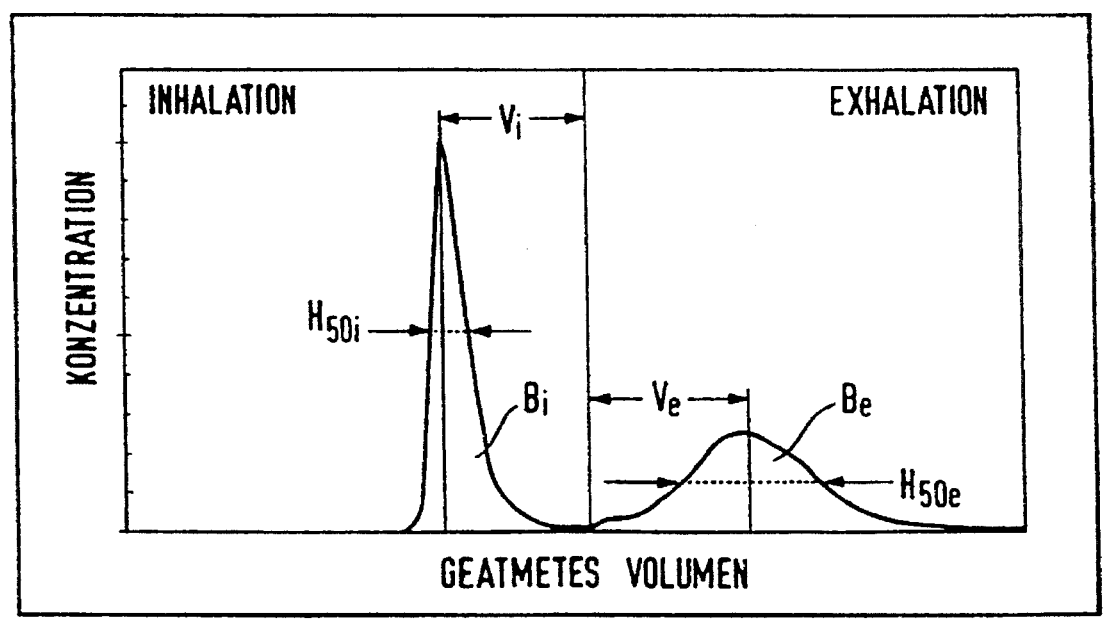
FIG. 8B another diagram illustrating known principles from the field of lung function diagnostics.

FIG. 6 shows a second preferred embodiment of the invention in a cross-sectional view. In this application many details about the arrangement and development of the control valves, the supply lines and a special construction of the breathing channel are shown.

In the center of FIG. 6 the flow FIG. 5 is shown in the vertical breathing channel 2 which is shown in a plug-in tube 11. A mounting drilling 12 into which the tube 11 is inserted is in valve block 1. The tube 11 has openings at the corresponding positions for the air channel 3 and the aerosol channel 4. Since the flow FIG. 5 and also the nonreturn valve below it are firmly connected with the tube 11, the important parts which must be disinfected can easily be removed from the assembly. The first drillings 13a and 13b in valve block 1 which run perpendicular to the plane of the drawing are meant for safety bolts which hold the tube 11 to the edges extending into the drillings.

The second drillings 14a and 14b in the valve block which run perpendicular to the plane of the drawing are meant for PTC heating elements which heat the valve block 1 in order to prevent condensation effects.

The longitudinal axis of the air channel 3 lies in front of the plane of the drawing in FIG. 6, whereby the longitudinal axis of the aerosol channel 4 lies behind the plane of the drawing so that neither longitudinal axis is shown. However, both longitudinal axis are, as in the first application shifted on both sides of the breathing channel 2 so that a tangential flow against the flow figure in its conical zone is achieved. On the side opposite the breathing channel, both supply channels 3 and 4 enter into a first and second space 15a and 15b in which there is each a valve element 16a and 16b for the movable first and second control valve S1 and S2 respectively. Both supply channels also enter into the third and fourth drilling 17a and 17b in the valve block 1 which serve as supply lines for the air and aerosol respectively. Pneumatic drive units 18a and 18b, situated on the outside of valve block 1, move both valve elements 16a and 16b. The pneumatic drive units are connected to the valve elements 16a and 16b via a cover 19a and 19b for the first and second spaces 15a and 15b respectively.

According to the second embodiment, the opening 2b of the breathing channel 2 is closed by a cover 19c through which a drive unit 18c of a third control valve S3 is connected to the corresponding valve element 16c. A fifth drilling 17c in valve block 1, perpendicular to the plane of the drawing, opens into a third space 15c in which the valve element 16c of the third control valve S3 is located and is movable. This third space 15c is for the breathed air during exhalation.

The operation of the second embodiment corresponds for the most part with that of the first which is described together with FIG. 4. The third control valve S3 is usually open and is only closed during the deep inhalation process $E_t$ and the following breath holding P.

Figure 7:
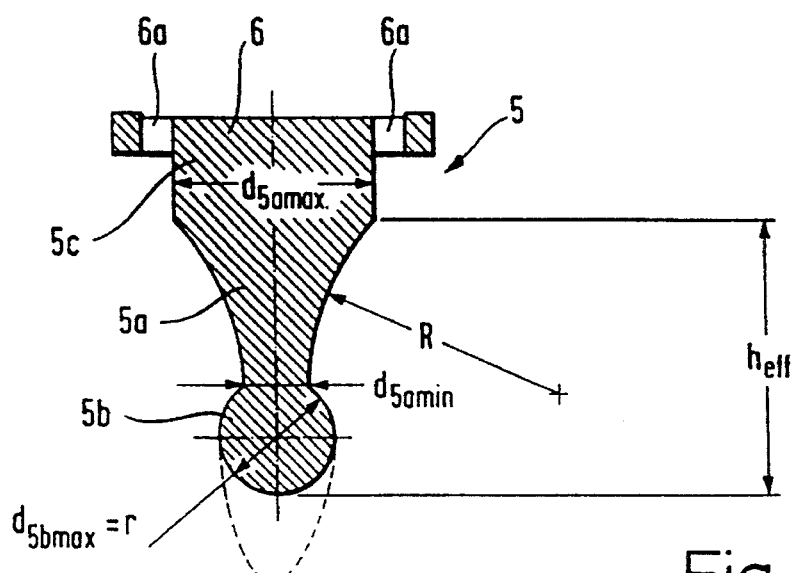
FIG. 7 a cross-sectional view of the flow figure of the first and second applications.

FIG. 7 shows an exemplary flow FIG. 5. Based on this example, the possibility of profiling, specifically of the conical portion 5a is to be explained. The following ratio specifications are based on measurements which were done during the development of the assembly with supply channels running perpendicular to the breathing channel and represent preferred orders of magnitude.

The conical portion 5a of the flow figure is formed by an arc that starts at the cylindrical portion 5c and has a radius R. Preferably, the ratio $R/D_{5amax}$ lies between 0.5 and 2.8. The expanded portion 5b is a ball with a radius r which is chosen so that the ratio r/R is between 0.2 and 0.7. The position of the expanded portion 5b is determined by the effective height $h_{eff}$ of the flow FIG. 5 which corresponds to the longitudinal extension of the conical portion 5a and the expanded portion 5b. The ratio $h_{eff}/r$ is 0.85 to 1.3.

The design of the expanded portion 5b of the flow FIG. 5 is especially advantageous as an axially symmetrical flow airfoil which gradually tapers in the direction of flow from its maximum diameter (dashed contour in FIG. 7). This contour can also be approximated by an ellipsoid.

The flow FIG. 5 as per FIG. 7 is one piece with the flat carrier 6 by which the flow figure is attached to the breathing channel. Also shown in FIG. 7 are the slits 6a for the breathed air during exhalation.

What is claimed is:

1. An assembly for producing aerosol pulses, said assembly comprising:
   a valve block having a breathing channel, an air channel which opens transversely into said breathing channel and an aerosol channel which also opens transversely into said breathing channel, each of said channels having a longitudinal axis, the longitudinal axis of said air channel being laterally shifted relative to the longitudinal axis of said aerosol channel;
   at least one control valve located in said valve block for controlling the supply of air and aerosol through said breathing channel, said air channel and said aerosol channel;
   a flow figure located in said breathing channel in an area of intersection of said air channel and said aerosol channel with said breathing channel in such a way that fluid flows through said air channel and said aerosol channel and tangentially strikes said flow figure.

2. An assembly as in claim 1, wherein said flow figure has a conical portion with a narrow end pointing in the direction fluid flows through said breathing channel during inhalation.

3. An assembly as in claim 2, wherein the flow figure has an expanded portion disposed at the narrow end of said conical portion.

4. An assembly as in claim 3, wherein said expanded portion is spherical.

5. An assembly as in claim 3, wherein said expanded portion is ellipsoidal.

6. An assembly as in claim 3, wherein said conical portion continuously and smoothly blends into said expanded portion.

7. An assembly as in claim 3, wherein said conical portion has a maximum diameter and a minimum diameter, and wherein said expanded portion has a diameter which is less than said maximum diameter but greater than said minimum diameter.

8. An assembly as in claim 7, wherein said expanded portion is spherical.

9. An assembly as in claim 7, wherein said expanded portion is ellipsoidal.

10. An assembly as in claim 7, wherein said conical portion continuously and smoothly blends into said expanded portion.

11. An assembly as in claim 7, wherein said flow figure has a cylindrical portion and an opposite end from said conical portion, and wherein the diameter of said cylindrical portion is the same as said maximum diameter of said conical portion.

12. An assembly as in claim 7, wherein said maximum diameter of said conical portion is less than a diameter of said breathing channel, and wherein a flat carrier which supports said flow figure is located in said breathing channel, said flat carrier having a diameter which is substantially the same as the diameter of said breathing channel and having arched slits formed therein in an area beyond said flow figure, wherein a thin elastic disk located on the side of the flat carrier opposite from the flow figure closes said slits during inhalation and at rest.

13. An assembly as in claim 1, wherein said longitudinal axis of said air channel and said longitudinal axis of said aerosol channel are essentially perpendicular to said longitudinal axis of said breathing channel.

14. An assembly as in claim 1, wherein said air channel and said aerosol channel are positioned symmetrically on opposite sides of said longitudinal axis of said breathing channel.

15. An assembly as in claim 1, wherein said flow figure is mounted in a tube which is insertable into said valve block and which encloses said breathing channel, said valve block having first and second drillings for receiving safety bolts for positioning said tube.

16. An assembly as in claim 15, further comprising PTC heating elements fitted within third and fourth drillings within said valve block.

* * * * *